(12) United States Patent
Boyle et al.

(10) Patent No.: US 9,302,085 B2
(45) Date of Patent: Apr. 5, 2016

(54) METHODS AND COMPOSITIONS FOR FACILITATING ARTERIAL ACCESS

(75) Inventors: Andrew Boyle, San Francisco, CA (US); David Majure, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 310 days.

(21) Appl. No.: 12/712,636

(22) Filed: Feb. 25, 2010

(65) Prior Publication Data

US 2010/0234828 A1 Sep. 16, 2010

Related U.S. Application Data

(60) Provisional application No. 61/159,358, filed on Mar. 11, 2009.

(51) Int. Cl.

| A61M 5/00 | (2006.01) |
|---|---|
| A61K 31/04 | (2006.01) |
| A61K 9/70 | (2006.01) |
| A61M 35/00 | (2006.01) |
| A61K 31/167 | (2006.01) |
| A61K 31/21 | (2006.01) |
| A61K 45/06 | (2006.01) |
| A61F 13/40 | (2006.01) |
| A61M 5/42 | (2006.01) |
| A61M 25/01 | (2006.01) |

(52) U.S. Cl.
CPC .............. *A61M 35/00* (2013.01); *A61K 31/04* (2013.01); *A61K 31/167* (2013.01); *A61K 31/21* (2013.01); *A61K 45/06* (2013.01); *A61M 35/006* (2013.01); *A61M 5/422* (2013.01); *A61M 5/425* (2013.01); *A61M 25/01* (2013.01)

(58) Field of Classification Search
CPC ..... A61K 31/04; A61K 31/167; A61K 31/21; A61K 45/06; A61K 25/01; A61K 2300/00; A61M 35/006; A61M 35/00; A61M 5/425; A61M 5/422
USPC .......................................................... 424/449
See application file for complete search history.

(56) References Cited

U.S. PATENT DOCUMENTS

| 5,202,125 | A |  | 4/1993 | Ebert et al. | |
|---|---|---|---|---|---|
| 5,620,416 | A |  | 4/1997 | Riviere et al. | |
| 5,750,141 | A |  | 5/1998 | Roberts et al. | |
| 2002/0006435 | A1 | * | 1/2002 | Samuels et al. | 424/449 |
| 2005/0202073 | A1 | * | 9/2005 | Jackson et al. | 424/449 |

FOREIGN PATENT DOCUMENTS

WO WO 2008109124 A1 * 9/2008

OTHER PUBLICATIONS

Zeiher et al. (1984). "The effect of various cutaneously administered nitroglycerin preparations on coronary heart disease". Schweiz Med Wochenschr Suppl., 16: 70-76 (abstract only).*
Stedman's Online—"blood vessel". [Retrieved on Apr. 1, 2013]. Retrieved from the internet <URL http://www.stedmansonline.com/content.aspx?id=mlrB1200003263&termtype=t>.*
Vasquez et al (2003). "Resolution of Peripheral Artery Catheter-induced Ischemic Injury Following Prolonged Treatment with Topical Nitroglycerin Ointment in Newborn: A Case Report". Journal of Perinatology, 23: 348-350.*
Gunawardene, et al., Local application of EMLA and glyceryl trinitrate ointment before venepuncture., Anaesthesia vol. 45 Issue 1, pp. 52-54, 1990.
Michael, et al., The application of EMLA and glyceryl trinitrate ointment prior to venepuncture. Anaesthesia Intensive Care, 1996, vol. 24, p. 360-364.
O'Hara, Jr., et al., Effects of topical nitroglycerin and intravenous lidocaine on propofol-induced pain on injection., Anesthesia & Analgesia, 1997, vol. 84, p. 865-869.
Sen, et al., The analgesic effect of nitroglycerin added to lidocaine on intravenous regional anesthesia. Anesthesia & Analgesia, 2006, vol. 102, p. 916-920.
Teillol-Foo, et al., Topical glyceryl trinitrate and eutectic mixture of local anaesthetics in children. A randomised controlled trial on choice of site and ease of venous cannulation., Anaesthesia. Oct. 1991;46(10):881-884.
Coppola et al., "Nitroglycerin, Nitroprusside, or Both, in Preventing Radial Artery Spasm during Transradial Artery Catheterization," Journal of Invasive Cardiology, 18(4):155-158 (2006).
Moe et al., "Influence of Skin Site on Bioavailability of Nitroglycerin Ointment in Congestive Heart Failure," Amer. J. Med., vol. 81, No. 5, pp. 765-770 (1986).
Griffin, The Textbook of Pharmaceutical Medicine, 6th ed., John Wiley & Sons Ltd., pp. 170 (1998).
Arbique, J.C., Venipuncture: Part I, Anatomy of the Arm and Vein Location (Jan. 2008), ARO Training & Consulting, 21 pages.

* cited by examiner

*Primary Examiner* — Brian-Yong Kwon
*Assistant Examiner* — Doan Phan
(74) *Attorney, Agent, or Firm* — Rudy J. Ng; Carol L. Francis; Bozicevic, Field & Francis LLP

(57) ABSTRACT

Provided are methods and compositions for locally increasing arterial diameter and providing local anesthesia in a subject. The methods include applying to a skin site of the subject a topical composition that includes a vasodilation agent and an anesthetic agent in a manner sufficient for locally increasing arterial diameter and providing local anesthesia in the subject. In some embodiments, the method includes inserting a cannula into an artery at the skin site of the subject. Also provided are topical compositions that find use in performing the subject methods.

22 Claims, 4 Drawing Sheets

METHODS AND COMPOSITIONS FOR FACILITATING ARTERIAL ACCESS

CROSS-REFERENCE TO RELATED APPLICATION

Pursuant to 35 U.S.C. §119(e), this application claims priority to the filing date of U.S. Provisional Patent Application Ser. No. 61/159,358, filed Mar. 11, 2009, which application is incorporated herein by reference in its entirety.

INTRODUCTION

Cannulation is an invasive medical procedure in which a tube (e.g., a cannula or a catheter, etc.) is inserted into a bodily cavity, duct, or vessel to drain fluid, measure pressure or administer a substance such as a medication. Arterial cannulation, where a cannula is inserted into an artery of a subject, can be used for continuous measurement of blood pressure (e.g., mean arterial pressure), repeated arterial blood gas measurement (e.g., for patients requiring non-invasive ventilation or intermittent positive-pressure ventilation (IPPV)), or repeated blood chemistry/hematology measurements. Possible access sites for arterial cannulation include the radial artery, the femoral artery, the brachial artery, and the dorsalis pedis artery.

Continuous invasive arterial blood pressure (BP) monitoring is used for assessment of high-risk patients in intensive care units (ICU) and operating rooms (OR). The radial artery on the inner aspect of the wrist is the most common site for insertion of the arterial lines. It is estimated that at least 5 million radial arterial lines are inserted annually in the United States, with over 10 million inserted annually world-wide. Three factors that make radial artery cannulation difficult are: small size of the radial artery, arterial spasm and pain. The small size of the radial artery makes it difficult to cannulate. In addition, the radial artery has the potential for spasm, particularly if multiple attempts are made to insert the arterial line. Spasm of the artery can make it even smaller and more difficult to access. Furthermore, the deep location of the radial artery and the surrounding nerves can lead to pain during cannulation, and local anesthesia may be required before insertion of the cannula.

In addition to invasive blood pressure monitoring, radial arterial access is also used for cardiac catheterization. Currently this approach is used in about 1% of the 1.1 million procedures performed annually in the United States, and the use of this procedure is increasing. Furthermore, radial access is used commonly (e.g., in up to 90% of cases) in some European countries, and there are 1.9 million cardiac catheterizations performed annually in Europe.

SUMMARY

Provided are methods and compositions for locally increasing arterial diameter and providing local anesthesia in a subject. The methods include applying to a skin site of the subject a topical composition that includes a vasodilation agent and an anesthetic agent in a manner sufficient for locally increasing arterial diameter and providing local anesthesia in the subject. In some embodiments, the method includes inserting a cannula into an artery at the skin site of the subject. Also provided are topical compositions that find use in performing the subject methods.

Aspects of the present disclosure include methods for locally increasing arterial diameter and providing local anesthesia in a subject that include applying to a skin site of the subject a topical composition that includes a vasodilation agent and an anesthetic agent in a manner sufficient for locally increasing arterial diameter and providing local anesthesia in the subject.

In some instances, the method further includes inserting a cannula into an artery at the skin site of the subject. In certain embodiments, the artery is a radial artery of the subject.

In some cases, the vasodilation agent is present in an amount sufficient for locally increasing arterial diameter in the subject. In certain embodiments, the vasodilation agent includes nitroglycerin.

In certain cases, the anesthetic agent is present in an amount sufficient for providing local anesthesia in the subject. In some instances, the anesthetic agent includes lidocaine.

Additional aspects of the present disclosure include methods for inserting a cannula into an artery of a subject, where the method includes applying to a skin site of the subject a topical composition comprising a vasodilation agent and an anesthetic agent in a manner sufficient for locally increasing arterial diameter and providing local anesthesia in the subject; and inserting the cannula into the artery of the subject.

In certain instances, the artery is a radial artery of the subject. In addition, in some embodiments, the applying is for a period of time of 30 minutes or more.

Aspects of the present disclosure also include a topical composition for locally increasing arterial diameter and providing local anesthesia in a subject. The topical composition can include a vasodilation agent in an amount sufficient for locally increasing arterial diameter in the subject, and an anesthetic agent in an amount sufficient for providing local anesthesia in the subject.

In certain embodiments, the topical composition can be formulated as a lotion, cream, paste, ointment, gel or foam. In some cases, the topical composition includes a transdermal patch. The transdermal patch can include an active agent layer. Additionally, in certain instances, the active agent layer includes a mixture that includes the vasodilation agent and the anesthetic agent. In certain cases, the active agent layer includes a first layer and a second layer, where the first layer includes the vasodilation agent and the second layer includes the anesthetic agent. In addition, the transdermal patch can further include a backing layer, and in some cases, further include an adhesive.

Additional aspects of the subject disclosure include kits for inserting a cannula into an artery of a subject. In certain embodiments, the kit includes a topical composition for locally increasing arterial diameter and providing local anesthesia in the subject, the topical composition including: a vasodilation agent in an amount sufficient for locally increasing arterial diameter in the subject; an anesthetic agent in an amount sufficient for providing local anesthesia in the subject. In addition, the kit includes a sterile cannula.

In certain embodiments, the kit further includes sterile packaging. Additionally, in some cases, the kit further includes a sterile wipe.

Figure 1:
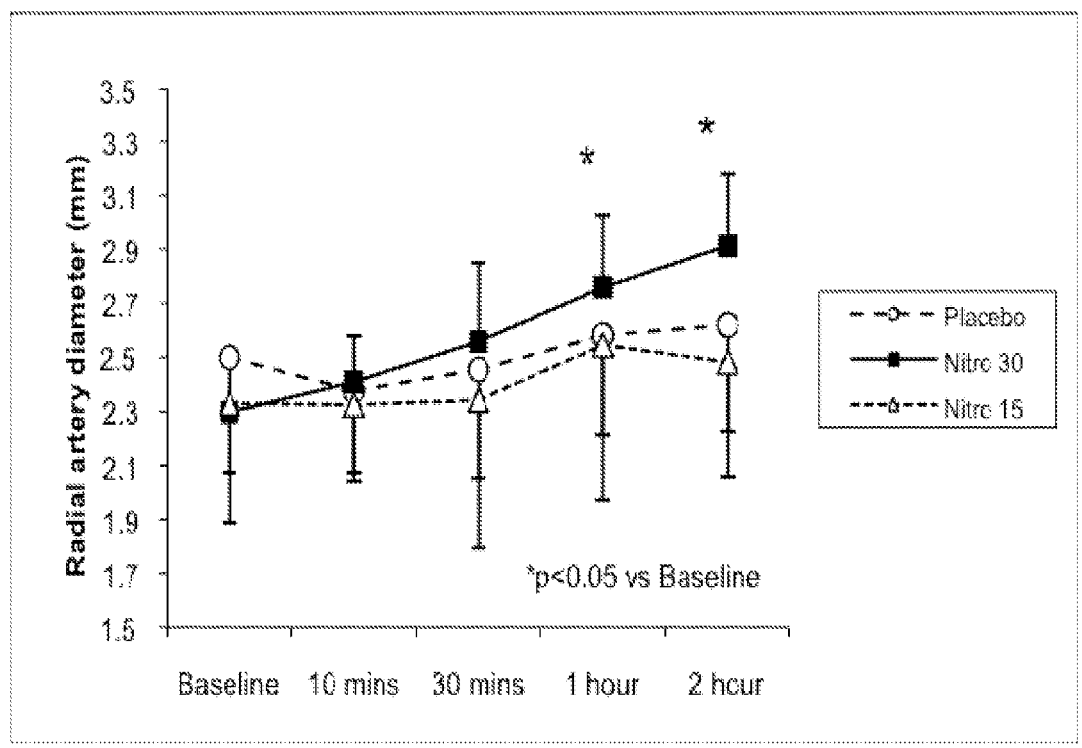
FIG. 1 provides a graph of radial artery diameter versus time for the topical application of 15 mg of nitroglycerin, 30 mg of nitroglycerin, and placebo. The 30 mg dose of nitroglycerin resulted in significant vasodilation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is to be understood that where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

DETAILED DESCRIPTION

Provided are methods and compositions for locally increasing arterial diameter and providing local anesthesia in a subject. The methods include applying to a skin site of the subject a topical composition that includes a vasodilation agent and an anesthetic agent in a manner sufficient for locally increasing arterial diameter and providing local anesthesia in the subject. In some embodiments, the method includes inserting a cannula into an artery at the skin site of the subject. Also provided are topical compositions that find use in performing the subject methods.

The subject topical compositions can facilitate arterial access by locally increasing arterial diameter and providing local anesthesia in a subject. In some cases, the topical composition may also facilitate a local reduction in the risk of arterial spasm. Arterial spasm is a temporary, sudden contraction of the muscles in the wall of an artery that can slow or stop blood flow through the artery. Reducing the risk of arterial spasm can allow for easier access to the artery, such as by facilitating easier insertion of a cannula into the artery of the subject by a health care professional (e.g., a nurse, doctor, surgeon, etc.).

Various aspects of embodiments of the subject topical compositions are described first in greater detail. Next, embodiments of methods in which the subject topical compositions may find use are reviewed in greater detail.

Topical Compositions

The present disclosure provides topical compositions for administering an active agent to a subject to facilitate arterial access. The terms "active agent" and "drug", as used herein, refer to a compound or composition of matter which, when administered to a subject (e.g., human or animal) induces a desired pharmacologic and/or physiologic effect.

As used herein, the term "topical composition" refers to any vehicle suitable for providing delivery of an active agent to a subject through the skin surface. Topical compositions can be applied to the skin surface of the subject and can provide for drug delivery through the skin to an underlying tissue adjacent the skin site in the subject. By "topical" drug delivery is meant administration of a drug to a skin site of a subject so that the drug is in contact with the skin site. In some cases, topical drug delivery includes maintaining an effective concentration of the active agent (e.g., anesthetic agent and/or vasodilation agent) in contact with the skin site for an extended period a time, which can be prior to, during, or after the arterial access procedure; e.g., to facilitate arterial access and minimize the pain of the subject during the arterial access procedure, and/or for an extended period thereafter. Topical drug delivery according to certain embodiments of the methods of the present disclosure provides for an effect (e.g., increase in arterial diameter, reduction in pain, and/or reduction in the risk of arterial spasm) at the local area where the active agents are administered, without detectable systemic physiologic effect of the drug on the subject.

Topical compositions of the present disclosure are suitable for providing local effects of the active agents included in the topical compositions. By "local" is meant that an active agent is administered to a subject such that the active agent's effects are at a limited area of tissue (e.g., the application site and adjacent underlying tissue area), rather than a general or systemic effect throughout the subject. For example, local anesthesia may involve the injection or application of an anesthetic agent to a specific area of the body, as opposed to the entire body and brain as occurs during general anesthesia.

The subject topical compositions include active agents for facilitating arterial access in a subject and providing local anesthesia during an arterial access procedure. In some instances, the active agents include a vasodilation agent in an amount sufficient for locally increasing arterial diameter in the subject, and an anesthetic agent in an amount sufficient for locally reducing pain in the subject. In addition, the vasodilation agent may also facilitate a reduction in the risk of arterial spasm in the subject. Thus, the vasodilation agent may be present in the topical composition in an amount sufficient for locally reducing the risk of arterial spasm in the subject.

By "sufficient amount" or "effective amount" is meant a nontoxic but useful amount of an active agent (e.g., vasodilation agent and/or anesthetic agent) given to a subject to provide the desired effect (e.g., increase in arterial diameter, local anesthesia, and/or reduction in the risk of arterial spasm). In some instances, the desired effect may be causing a condition to occur. For example, a sufficient amount of a vasodilation agent will be a dosage effective for causing an increase in arterial diameter in the subject. In some cases, the desired effect may be a reduction in the risk of occurrence of a condition, where reduction is used in a broad sense to refer to at least a decrease in the magnitude of a parameter associated with a procedure, such as the degree of pain, or the frequency or severity of arterial spasm that may occur during an arterial access procedure. The effect may be prophylactic in terms of completely or partially preventing a condition and/or adverse affect attributable to the condition. For example, a sufficient amount of an anesthetic agent will be a dosage effective for providing local anesthesia in the subject. In addition, a sufficient amount of a vasodilation agent may include a dosage effective to reduce the risk of arterial spasm that can result from attempts to access an artery. The effective amount may vary with the nature of the skin site, the severity of the condition being treated, the duration of the treatment, the nature of any concurrent treatment, the pharmaceutically acceptable carrier used if any, the age and physical condition of the subject, and analogous factors within the knowledge and expertise of those skilled in the art.

As indicated above, the subject active agents may include a vasodilation agent for locally increasing arterial diameter in a subject. Vasodilation agents relax smooth muscle cells in arteries and thereby facilitate an increase in arterial diameter. Suitable vasodilation agents include, but are not limited to: nitric oxide inducers, such as nitroglycerin (also known as glyceryl trinitrate), isosorbide mononitrate, isosorbide dinitrate, pentaerythritol tetranitrate (PETN), sodium nitroprusside, amyl nitrates, and the like; calcium channel blockers, such as verapamil, diltiazem, nifedipine, amlodipine, nicardipine, felodipine, and the like; phosphodiesterase type 5 (PDE5) inhibitors, and the like; theobromide; papaverine; magnesium; combinations thereof; and the like. Vasodilation agents of interest also include pharmacologically acceptable salts, bases, esters, amides, derivatives or prodrugs thereof.

In certain embodiments, the vasodilation agent of the subject topical compositions includes nitroglycerin. In some instances, nitroglycerin is included in the topical composition in an amount sufficient for locally increasing arterial diameter in the subject. By "increasing arterial diameter" is meant an increase in the average diameter of an artery of a subject, as assessed by arterial diameter assessment tools (e.g., ultrasound) as are known in the art. An "increase in arterial diameter of 25% or more", for example, means that the average diameter of an artery of the subject increases by 25% or more from an initial diameter, as assessed by any of the suitable arterial diameter assessment methods disclosed in greater detail below.

In some embodiments, the vasodilation agent may locally increase arterial diameter by 5% or more, 10% or more, 15% or more, 20% or more, 25% or more, 30% or more, 35% or more, or 40% or more, when compared to arterial diameter in the absence of the vasodilation agent, as measured by any arterial diameter assessment method known to those of skill in the art, discussed in more detail below.

Additionally, the relaxation of smooth muscle cells in arteries may also facilitate a reduction in the risk of arterial spasm. Thus, in some cases, nitroglycerin may be included in the topical composition in an amount sufficient for locally reducing the risk of arterial spasm in the subject. By "reducing the risk of arterial spasm" and "reduction in the risk of arterial spasm" is meant a decrease in the frequency or severity of arterial spasm experienced by a subject, as assessed by arterial spasm assessment techniques as are known in the art and as are discussed below. A "reduction in the risk of arterial spasm of 50% or more", for example, means arterial spasm occurs with a frequency or severity that is less than half that occurs in the absence of the subject topical composition, as assessed by any suitable arterial spasm assessment methods, such as visual inspection, palpation, etc., as described in detail below.

In some embodiments, the vasodilation agent may locally reduce the risk of arterial spasm by 5% or more, 10% or more, 15% or more, 20% or more, 25% or more, 30% or more, 35% or more, 40% or more, 45% or more, 50% or more, 60% or more, 70% or more, 80% or more, 90% or more, 95% or more, or 99% or more, when compared to the amount of arterial spasm in the absence of the vasodilation agent, as measured by any arterial spasm assessment method known to those of skill in the art, discussed in more detail below.

Anesthetic agents suitable for use in the subject topical compositions may include, but are not limited to, lidocaine, lignocaine, benzocaine, procaine, marcaine, prilocalne, bupivacaine, levobupivacaine, tetracaine, mepivacaine, ropivacaine, etidocaine, chloroprocaine, propoxycaine, cyclomethylcaine, dimethylcaine, cocaine, cocaine hydrochloride, butanilicaine, trimecaine, dibucaine, dyclonine hydrochloride, promazine, pramoxine hydrochloride, proparacaine hydrochloride, benoxinate hydrochloride, proprionic acid derivatives, fenamates, pyrrolealkanoic acids, pyrazolone derivatives, oxicams, pramoxine, butamben picrate, butamben oil, clove oil, eugenol, combinations thereof, and the like. See e.g., Remington: The Science and Practice of Pharmacy, 21st Edition, Philadelphia, Pa., Lippincott Williams & Wilkins, 2005, for descriptions of the compositions and uses thereof. For example, the subject topical compositions can include combinations of a long-acting anesthetic agent (e.g., an anesthetic agent with a half-life ($t_{1/2\alpha}$) of more than one hour, such as bupivacaine, etidocaine, etc.) and a short-acting anesthetic agent (e.g., an anesthetic agent with a half-life ($t_{1/2\alpha}$) of one hour or less, such as lidocaine, prilocalne, mepivacaine, etc.). As used herein, anesthetic agents also include pharmacologically acceptable salts, bases, esters, amides, derivatives or prodrugs thereof.

In certain cases, the anesthetic agent of the subject topical compositions includes lidocaine. Lidocaine may be included in the topical composition in an amount sufficient for providing local anesthesia in the subject. By "local anesthesia" is meant a decrease in the amount of pain otherwise associated with an arterial access procedure, as assessed by pain assessment methods as are known in the art. For example, a "pain reduction of 50% or more" means that the subject experiences and/or reports a level or severity of pain that is less than half of the level of pain experienced by the subject in the absence of the topical composition, as assessed by any suitable pain assessment method, as described in detail below. Alternatively, a reduction in pain could mean a reduction in the number of patients who experience pain to a certain threshold. For example, a "pain reduction of 50% or more" may refer to a number of patients that is half or less than half the number of patients who experience pain to a certain threshold in the absence of the topical composition.

In some embodiments, the anesthetic agent may locally reduce pain of an arterial access procedure by 10% or more, 20% or more, 30% or more, 40% or more, 50% or more, 60% or more, 70% or more, 80% or more, 90% or more, 99% or more, when compared to the amount of pain the subject experiences and/or reports in the absence of the anesthetic agent, as measured by any pain assessment method known to those of skill in the art, discussed in more detail below. For example, on a numerical scale from 0 to 10 pain units for assessing pain, the anesthetic agent may locally reduce pain of an arterial access procedure by 1 or more pain units, 2 or more, 3 or more, 4 or more, 5 or more, 6 or more, 7 or more, 8 or more, 9 or more pain units, when compared to the amount of pain the subject experiences and/or reports in the absence of the anesthetic agent.

The vasodilation agent and the anesthetic agent can be applied to the skin site separately or as a mixture. If the vasodilation agent and the anesthetic agent are applied separately, then they can be provided as individual topical compositions, such as a first topical composition and a second topical composition, where the first topical composition includes the vasodilation agent and the second topical composition includes the anesthetic agent. In certain embodiments, the first and second topical compositions are applied to adjacent skin sites of the subject, such that the local effects of the vasodilation agent and the anesthetic agent provide for an increase in arterial diameter and local anesthesia at the desired arterial access site. Alternatively, the first and second topical compositions may be applied in sequence such that the second topical composition is applied over the first topical composition. In other cases, the first topical composition may be applied over the second topical composition.

In certain instances, the vasodilation agent and the anesthetic agent are provided as a topical composition that includes a mixture of the vasodilation agent and the anesthetic agent in a single topical composition. In these instances, application of the topical composition to a skin site of a subject administers the vasodilation agent and the anesthetic agent to the subject substantially simultaneously. The vasodilation agent and the anesthetic agent can be mixed prior to administration or can be mixed in situ at the desired skin site.

Formulations of the subject topical compositions may include, but are not limited to, solutions, suspensions, emulsions, etc. For example, the subject topical compositions may be formulated as a cream, lotion, foam, ointment, paste, gel, applicator stick, paint, powder, aerosol spray, liniment, and the like. Where desired, topical compositions may include a covering optionally applied thereto to facilitate maintaining the topical composition at the desired skin site while minimizing transfer of the topical composition to undesired locations. Thus, in some embodiments, the subject topical compositions may be incorporated with, or used at the same time as a dressing, including but not limited to gauze, mesh, absorbent padding, adhesive bandages, and the like.

The amount of topical composition applied to the skin site of a subject may vary. For example, where the topical composition is applied to a skin site prior to arterial access, the area of skin covered by the applied topical composition can range from 1 cm$^2$ to 50 cm$^2$, such as from 1 cm$^2$ to 20 cm$^2$, including from 5 cm$^2$ to 10 cm$^2$. In certain embodiments, the topical compositions include a vasodilation agent, such as nitroglycerin, where the amount of the vasodilation agent ranges from 1.5 mg to 75 mg, such as from 7.5 mg to 60 mg, including from 15 mg to 45 mg, for example from 22.5 mg to 37.5 mg. In some instances, the amount of the vasodilation agent is 15 mg. In some cases, the amount of the vasodilation agent is 30 mg. Certain embodiments of the subject topical compositions include an anesthetic agent, such as lidocaine, where the amount of the anesthetic agent ranges from 10 mg to 100 mg, such as from 10 mg to 50 mg, including from 20 mg to 40 mg. In some instances, the amount of the anesthetic agent is 20 mg. In some cases, the amount of the anesthetic agent is 40 mg. In certain embodiments, the amount of the anesthetic agent is 25 mg. In some instances, the amount of the anesthetic agent is 50 mg. The dosage required to produce the desired anesthetic effect depends on the anesthetic agent used and may be higher or lower than an effective dose of lidocaine. Determination of the appropriate dose for the vasodilation agent and the anesthetic agent is within the skill of one in the art given the parameters as disclosed herein. The dosage range can be determined by considering the active agent employed, the desired dose of active agent, the size of the skin area to be treated, the nature of the procedure, etc. Individual sensitivities of a subject can also influence the dosage amounts administered to the subject.

The topical composition may include more than one vasodilation agent and/or more than one anesthetic agent. In some instances, pharmaceutically acceptable analogs of such vasodilation agents and/or anesthetic agents can be used as well, including salts, bases, esters, amides, prodrugs or combinations or derivatives thereof.

The active agents of the subject topical compositions can be administered with one or more additional active agents. As used herein, "administered with" means that two or more active agents are administered at times sufficiently close that the results observed are indistinguishable from those achieved when the active agents are administered at the same point in time. The two or more active agents may be administered simultaneously (such as concurrently) or sequentially. Simultaneous administration may be carried out by mixing the two or more active agents prior to administration, or by administering the two or more active agents at the same point in time. Such administration may be at different anatomic sites (for example, at adjacent skin sites), or over substantially the same area of skin. The subject topical compositions can therefore optionally include, in addition to a vasodilation agent and an anesthetic agent, at least one additional active agent useful in causing a desired effect at the arterial access site without interfering with the effects of the vasodilation agent and the anesthetic agent. In some embodiments, the additional active agents provided in the topical compositions include, but are not limited to, antibiotic agents, anticoagulant agents, anti-inflammatory agents, procoagulants (e.g., protamine, thrombin, and the like), etc.

The subject topical compositions can also include a pharmaceutically acceptable carrier or any other necessary components of topical formulations and delivery devices, such as excipients, solubilizing agents, suspending agents, dispersing agents, preservatives, animal and vegetable fats, oils, or waxes, stabilizing agents, thickening or gelling agents, buffering agents, skin permeation enhancers, adhesive agents, coloring agents, or combinations thereof. Non-limiting examples of pharmaceutically acceptable components include, but are not limited to, any of the standard pharmaceutical carriers, such as phosphate buffered saline solutions, water, emulsions, such as oil/water emulsions or water/oil emulsions, microemulsions, and various types of wetting agents. Suitable nontoxic pharmaceutically acceptable carriers for use in the topical compositions of the present disclosure will be apparent to those skilled in the art of pharmaceutical formulations and examples are described in Remington: The Science and Practice of Pharmacy, 21st Edition, Philadelphia, Pa., Lippincott Williams & Wilkins, 2005. For example, the active agents of the subject topical compositions may be formulated with excipients (e.g., lanolin, white petrolatum, glycerol), preservatives (e.g., methylparaben), skin permeation enhancers (e.g., ethyl acetate, ethanol, dimethyl sulfoxide (DMSO)), coloring agents (e.g., amaranth), and the like, or combinations thereof. The choice of suitable carriers may depend on the particular dosage form desired, e.g., whether the active agents are to be formulated into a cream, lotion, foam, ointment, paste, gel, etc., as well as on the other active agent(s) that may be included in the topical composition.

Transdermal Patches

Transdermal patches are exemplary topical compositions for use in the methods disclosed herein. Transdermal patches are adhesive patches that include an active agent that are placed on the skin to deliver the active agent through the skin. Transdermal patches can deliver the active agent by percutaneous absorption, which is the absorption of substances through unbroken skin. After a transdermal patch is applied to the skin, the active agent contained in the patch is delivered topically to the local area where the transdermal patch is applied. Certain embodiments of the subject transdermal patches include active agents, such as a vasodilation agent in an amount sufficient for locally increasing arterial diameter in the subject, and an anesthetic agent in an amount sufficient for providing local anesthesia in the subject, as described in detail above.

Transdermal patches can include a backing layer. The backing layer may be flexible to an extent that it can be brought into close contact with a skin surface. The backing layer facilitates maintaining the active agents at the desired skin site while minimizing transfer of the active agents to undesired locations. In addition, the backing layer material can be selected such that it does not absorb the active agent to a significant degree, and does not allow the active agent to be released from the sides of the backing layer in a significant amount. The backing layer may include, but is not limited to, non-woven fabrics, woven fabrics, films (including sheets), polyvinyl chloride, polyethylene, synthetic rubber, porous bodies, foamed bodies, paper, composite materials obtained by laminating a film on a non-woven fabric or fabric, and combinations thereof.

The subject transdermal patches may include one or more active agent layers. In certain embodiments, the vasodilation agent and the anesthetic agent are provided in a single active agent layer. Thus, the transdermal patch may include an active agent layer, where the active agent layer includes the vasodilation agent and the anesthetic agent. In these embodiments, the vasodilation agent and the anesthetic agent may be mixed together in the active agent layer, or may be provided as distinct layers within the active agent layer. For example, the transdermal patch can include an active agent layer having a first layer and a second layer, where the first layer includes the vasodilation agent and the second layer includes the anesthetic agent. The first and second layers can be arranged such that the first layer is provided on the backing layer and the second layer is provided on the first layer. Alternatively, the first and second layers can be arranged such that the second layer is provided on the backing layer and the first layer is provided on the second layer. In yet other embodiments, the layers are arranged such that the first layer and the second layer are adjacent each other.

The transdermal patches may also include an adhesive. The adhesive can be provided as a separate adhesive layer. In some cases, the active agent layer includes the adhesive. The adhesive may be any adhesive suitable for use with transdermal patches known to those of skill in the art, such as, but not limited to: acrylic polymer adhesives; copolymers of various acrylate monomers, such as, but not limited to butyl acrylate, 2-ethylhexyl acrylate, methyl acrylate, ethyl acrylate, methyl methacrylate, etc.; copolymers of acrylate monomers and other monomers, such as, but not limited to, vinyl acetate, t-octyl acrylamide, etc.; and the like.

In some embodiments, the transdermal patches also include a release liner. The release liner is provided on the surface of the transdermal patch that is distal from the backing layer. The release liner facilitates the protection of the active agent layer prior to use. Before applying the transdermal patch onto a skin surface, the release liner may be removed, thereby exposing the active agent layer. In some cases, the release liner may include, but is not limited to, a polyethylene-coated paper, such as a polyethylene-coated wood free paper, polyolefin-coated glassine paper, a polyethylene terephthalate (polyester) film, a polypropylene film, or the like.

Additionally, in some embodiments, the transdermal patch can have a geometric shape that corresponds to the shape of the application site. Thus, the shape of the transdermal patch can be flat or three-dimensional, round, oval, square, and have concave or convex outer shapes, or the transdermal patch can be segmented by the user into a desired shape.

Methods

The subject topical compositions find use in a variety of methods for facilitating arterial access by locally increasing arterial diameter, providing local anesthesia, and in some instances reducing the risk of arterial spasm in a subject. Arterial access can be provided by any procedure familiar to those of skill in the art for gaining access to the interior of an artery of a subject, such as, but not limited to, insertion of a cannula (e.g., catheter, needle, sheath, tube, etc.), into the artery of the subject. Applications include, but are not limited to, continuous invasive blood pressure monitoring (e.g., mean arterial pressure), repeated arterial blood gas measurement (e.g., for patients requiring non-invasive ventilation or intermittent positive-pressure ventilation (IPPV)), repeated blood chemistry/hematology measurements, cardiac catheterization, other procedures where it is desirable to insert cannulae into an artery of a subject, and the like. Possible sites for arterial cannulation include the radial artery, the femoral artery, the brachial artery, the dorsalis pedis artery, etc.

Methods of using the topical compositions of the present disclosure may vary depending on the particular application. In certain embodiments, the methods include methods for inserting a cannula into an artery of a subject. During use, the topical compositions can be applied to a skin site of the subject, such as a skin site that is adjacent to or overlies an artery. The method by which the topical compositions are contacted with the skin site may also vary. For example, the topical compositions can be applied manually over a predetermined skin site, dispensed from a suitable dispenser, etc. In addition, the subject topical compositions may be formulated as a transdermal patch and applied to the skin site of the subject.

The methods of the present disclosure include the steps of applying topically to a skin site of a subject a vasodilation agent and an anesthetic agent in a manner sufficient for locally increasing arterial diameter and providing local anesthesia in the subject. As described above, in certain embodiments, the vasodilation agent is present in an amount sufficient for locally increasing arterial diameter in the subject, and the anesthetic agent is present in an amount sufficient for providing local anesthesia in the subject. In addition, the vasodilation agent may be present in an amount sufficient for locally reducing the risk of arterial spasm in the subject. Thus, the vasodilation agent and the anesthetic agent facilitate arterial access and provide local anesthesia at the site of application of the topical composition. The method may also include inserting a cannula into an artery at the skin site of the subject. In some instances, the artery is a radial artery on the subject.

Following application of the topical composition to the skin site of a subject, the method may include maintaining the topical composition at the skin site for a period of time sufficient to result in local anesthesia in a significant amount as compared to the amount of local anesthesia experienced by the subject in the absence of the topical composition. The assessment of pain in accordance with the methods of the present disclosure can include, but is not limited to, assessment tools such as the McGill Pain Questionnaire (MPQ), which can include a pain response index (PRI) and a present pain index (PPI), a visual analog scale (VAS) (pain scale as defined by Littman, G. S. et al., *Clin. Pharmacol. Ther.* 1985; 38:16-23), a numerical scale, a categorical scale, a pain faces scale, and the like. Similar pain assessment tools and surveys as known in the art may also be used. In some embodiments, pain assessment can also include objective measures as are known in the art such as measurement of physiological parameters such as blood pressure and pulse, or by using sensors to measure a physiological parameter, etc.

In assessing the degree of local anesthesia experienced by a subject, the amount of time between application of the topical composition and a significant local anesthetic effect, the degree of local anesthesia, and the duration of local anesthesia using the topical compositions and methods of the present disclosure can be evaluated. For example, the level of local anesthesia experienced by a subject can be assessed by comparing the level of pain at various time periods after administration of the subject topical compositions, such as after 15 minutes or more, 30 minutes or more, 60 minutes or more, 120 minutes or more, etc. to determine the point or range of time after administration of the topical composition that the subject experiences a minimum of pain of the arterial access procedure. For example, the subject may experience a minimum of pain for a period of time ranging from 15 min to 240 min, such as from 15 min to 180 min, including from 30 min to 120 min after applying the topical composition to the skin site of the subject. Thus, in certain embodiments, the method includes applying the topical composition for a period of time of 15 min or more, such as 30 minutes or more, including 60 min or more, for example 120 min or more before an arterial access procedure.

In addition, following application of the topical composition to the skin site of a subject, the method may include maintaining the topical composition at the skin site for a period of time sufficient to result in locally increasing arterial diameter in a statistically significant manner as compared to the arterial diameter of the subject in the absence of the topical composition. The assessment of arterial diameter can include techniques such as, but not limited to, ultrasound, X-ray, computed tomography (CT), magnetic resonance imaging (MRI), photoacoustic imaging, angiography, and the like. The assessment of arterial diameter can be performed before and/or after application of the topical composition to the skin site of a subject. In some cases, the arterial diameters can be compared between a skin site where the topical composition has been applied and another skin site where no topical composition or a placebo has been applied. Similar to the assessment of pain, the assessment of arterial diameter can be performed at various time periods after administration of the subject topical compositions, such as after 15 minutes or more, 30 minutes or more, 60 minutes or more, 120 minutes or more, etc. to determine the point or range of time after administration of the topical composition that the subject experiences a maximum increase in arterial diameter. For example, the subject may experience a maximum increase in arterial diameter for a period of time ranging from 15 min to 240 min, such as from 15 min to 180 min, including from 30 min to 120 min after applying the topical composition to the skin site of the subject.

In certain embodiments, method includes maintaining the topical composition at the skin site of a subject for a period of time sufficient to result in locally reducing the risk of arterial spasm in the subject in a statistically significant manner as compared to the amount of arterial spasm experienced by the subject during an arterial access procedure in the absence of the topical composition. In assessing the degree of arterial spasm experienced by a subject, the frequency, severity, and duration of arterial spasms can be evaluated, as well as the consequences of spasm, such as inability to access the artery. For example, the risk of arterial spasm in a subject can be assessed by comparing the occurrence of arterial spasm with and without application of the subject topical compositions. Alternatively, spasm can be quantified as the number of patients who do or do not experience any degree of spasm, and this can be compared between groups receiving the topical composition and those not receiving the topical composition (or those receiving a placebo).

The assessment of arterial spasm can include techniques such as, but not limited to, visual inspection, palpation, a numerical scale, a categorical scale, assessment of the success and/or ease of arterial access procedures, and the like. In some embodiments, arterial spasm assessment can also include objective measures as are known in the art such as measurement of physiological parameters such as blood pressure and pulse, or by using sensors to measure a physiological parameter, etc. Similar to the assessment of pain and arterial diameter, the assessment of arterial spasm can be performed at various time periods after administration of the subject topical compositions, such as after 15 minutes or more, 30 minutes or more, 60 minutes or more, 120 minutes or more, etc. to determine the point or range of time after administration of the topical composition that the subject experiences a minimum of arterial spasm.

In performing the methods of the present disclosure, the topical compositions can be applied to the subject before the arterial access procedure, in order to prevent or reduce the risk of occurrence of the symptoms (e.g., pain and/or arterial spasm). In addition, the subject topical compositions can be applied before the arterial access procedure to facilitate arterial access by locally increasing the arterial diameter in the subject. In certain cases, the subject topical compositions can be applied to the skin site 10 min or more, 15 min or more, 30 min or more, 1 hour or more, or 2 hours or more before the arterial access procedure. In certain embodiments, the subject topical compositions can be applied to the subject after the arterial access procedure to reduce the effect of symptoms after they have occurred (e.g., to treat arterial spasm once it has occurred). For example, arterial spasm can include situations where there is resistance or an inability to remove the arterial cannula due to severe arterial spasm.

As discussed above, methods of the present disclosure can be performed on the radial artery of a subject. For example, the subject topical compositions can be applied to the skin on the ventral side of the wrist in an amount sufficient for locally increasing radial arterial diameter, providing local anesthesia in the area of radial artery access, and in some cases, reducing the risk of spasm in the radial artery of the subject. These effects may allow for easier access to the radial artery during procedures, such as, but not limited to, radial artery cannulation, radial artery catheterization, and the like.

A variety of subjects are treatable according to the present methods. These subjects include "mammals", where this term is used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative aspects, the subjects will be humans.

Kits

Also provided are kits that find use in practicing the subject methods, where the subject kits at least include a topical composition, as described above. In certain embodiments, the kits further include a cannula. The subject topical composition in the kits may be present in a package. Kits may include the topical composition in an amount suitable for a single application (e.g., a unit dose, such as a single dose), or can be provided in an amount suitable for multiple applications. In instances in which the topical composition is present in a kit in an amount sufficient for more than one application, multiple packages (e.g., tube, bottle, dispenser, container, etc.) may be provided with each containing an amount of the topical composition for a single application. In other cases, the topical composition can be provided in a reusable package containing an amount sufficient for more than one application and an amount of topical composition sufficient for a single application can be used as desired.

The kits may include one or more packages containing the topical composition as a mixture of the vasodilation agent and the anesthetic agent. In these cases, the vasodilation agent and the anesthetic agent can be applied to the skin site of the subject substantially simultaneously. In other cases, the vasodilation agent and the anesthetic agent can be provided separately, such as in separate packages. In these cases, the vasodilation agent and the anesthetic agent can be applied to the skin site of the subject substantially simultaneously or sequentially. For example, the vasodilation agent and the anesthetic agent can be mixed prior to administration or can be mixed in situ at the desired skin site. In yet other embodiments, the vasodilation agent and the anesthetic agent can be provided in separate sections within the same package, where the package provides for mixing prior to administration or for side-by-side application of the vasodilation agent and the anesthetic agent.

The topical composition and cannula of the subject kits can be provided in sterile packaging, such that the topical composition and the cannula can be maintained in a sterile condition prior to use. The topical composition and cannula can be provided in individual sterile packages suitable for a single use. In addition, the packages can be disposable after a single use, such that each package is only used once and new sterile packages are used for subsequent applications. In some instances, the subject kits can further include sterile preparation components that may facilitate sterilization of the skin surface where the topical compositions are to be applied and where the arterial access procedure is to be performed. For example, sterile preparation components can include sterile wipes. The sterile wipes may be individually packaged for single use. In addition, the sterile wipes can include antiseptic agents, such as, but not limited to, ethanol, isopropyl alcohol, n-propanol, iodine, benzalkonium chloride (BAC), cetyl trimethylammonium bromide (CTMB), benzethonium chloride (BZT), hydrogen peroxide, triclosan, and the like. Other sterile components that may be included in the subject kits include, but are not limited to, syringes, needles, cannula, dressings, sterile trays, gloves, etc.

In certain embodiments, the topical composition included in the subject kits can be formulated as a transdermal patch. Kits can include one or more transdermal patches, where a single transdermal patch includes an amount of the topical composition sufficient for a single application. Thus, the transdermal patch can be applied to a skin site for a sufficient amount of time to cause the desired effects (e.g., an increase in arterial diameter, local anesthesia and, in some cases, reduction in the risk of arterial spasm), and then removed from the skin site and discarded.

The subject kits may also include instructions for how to use the topical compositions in methods for inserting a cannula into an artery of a subject. The instructions may include information about dosing, application times, how to use the packaged topical compositions, etc. In certain embodiments, the subject kits can include instructions on how to use the topical compositions for inserting a cannula into a particular artery, e.g., a radial artery. The instructions may be recorded on a suitable recording medium. For example, the instructions may be printed on a substrate, such as paper or plastic, etc. As such, the instructions may be present in the kits as a package insert, in the labeling of the container of the kit or components thereof (such as associated with the packaging or subpackaging), a website URL directing the user to a webpage which provides the instructions, etc. In other embodiments, the instructions may be present as an electronic storage data file present on a suitable non-transient computer readable storage medium, e.g., CD-ROM, DVD, diskette, flash memory, etc.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Experiments were performed to investigate the effects of combined topical administration of nitroglycerin and lidocaine on the radial artery diameter. In addition, experiments were performed to determine whether combined topical administration of nitroglycerin and lidocaine acted locally or systemically.

A dose escalation study of topical nitroglycerin was performed. Twenty healthy volunteers were selected based on the following inclusion criteria: willing and able to give written informed consent and comply with study requirements; and able to speak English. In addition, the subjects were selected based on the following exclusion criteria: presence or history of liver, cardiovascular, rheumatologic, cancer or renal disease; current treatment with any vasodilator therapy; systolic blood pressure of less than 90 mmHg; history of radial artery catheterization within the previous year; absence of radial artery blood flow in one or both arms; pregnancy; and active infection.

Each of the twenty selected subjects received either 15 mg or 30 mg of nitroglycerin (Nitro-Bid 2% ointment, 1 or 2 inches, E Fougera & Co, NY) applied to one wrist and a placebo (sorbolene cream) applied to the other wrist. Applications were performed as single-blind (subject) experiments. Radial artery diameter was measured with ultrasound before application of the topical compositions and at time intervals after application of the topical compositions. The subjects were tested again at a later date, where they received the alternate dose of nitroglycerin on one wrist and the placebo on the other wrist.

The experiments showed that administration of 15 mg of nitroglycerin did not significantly increase radial artery diameter compared to the placebo, but administration of 30 mg of nitroglycerin increased radial artery diameter by approximately 25% (FIG. 1). The increase in radial artery diameter was maintained during the 2-hour application. Topical application of nitroglycerin did not affect the diameter of the radial artery in the contralateral wrist, nor did it significantly affect the systemic blood pressure. Therefore, the effect of topical application of nitroglycerin was not systemic, but rather topical nitroglycerin acted locally on the radial artery.

Experiments were also performed to determine the effects of combined topical administration of nitroglycerin and lidocaine on the radial artery diameter. The same subjects received topical applications of nitroglycerin (30 mg) with either 20 mg or 40 mg of lidocaine topical cream (LMX 4%, Ferndale, Mich.). The nitroglycerin and lidocaine were applied at adjacent skin sites on the wrist.

Figure 2:
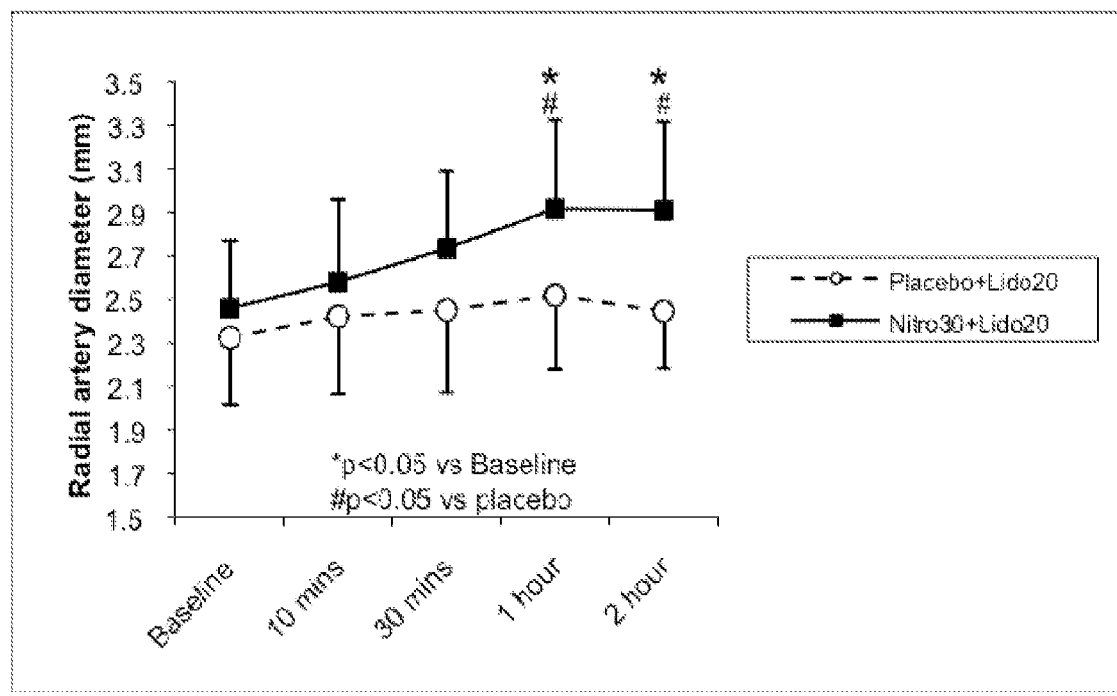
FIG. 2 provides a graph of radial artery diameter versus time for embodiments of the subject topical compositions that include 30 mg of nitroglycerin and 20 mg of lidocaine.
Figure 3:
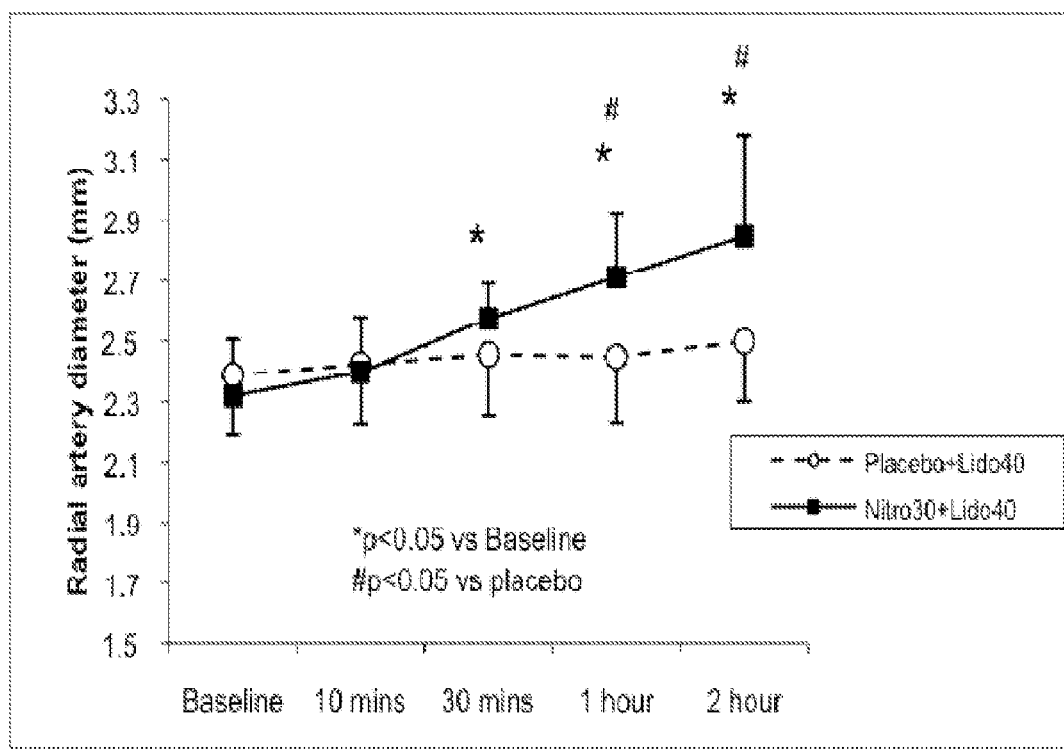
FIG. 3 provides a graph of radial artery diameter versus time for embodiments of the subject topical compositions that include 30 mg of nitroglycerin and 40 mg of lidocaine. Lidocaine alone had no appreciable effect on arterial diameter. The presence of lidocaine did not prevent the vasodilation caused by nitroglycerin.
Figure 4:
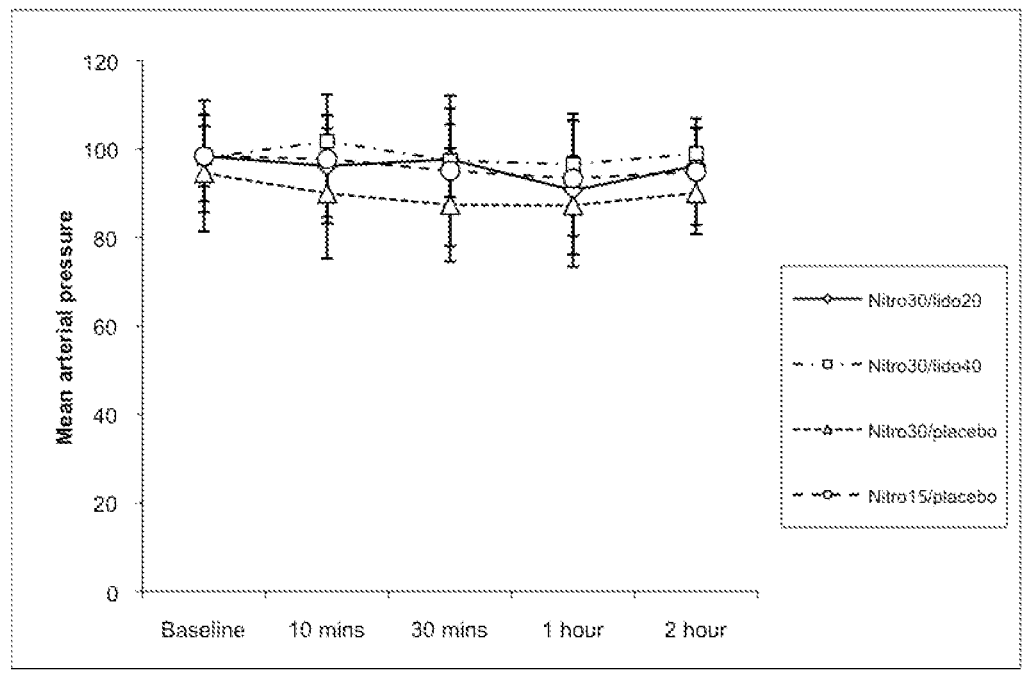
FIG. 4 provides a graph of mean arterial pressure versus time for embodiments of the subject topical compositions. There was no detectable or significant change in systemic blood pressure, indicating no significant systemic effect of the compounds.

The results showed that application of 20 mg or 40 mg of lidocaine had no detectable effect on the vasodilatory action of nitroglycerin (FIGS. 2 and 3). There was an approximate 25% increase in radial artery diameter with both doses of lidocaine indicating no physiologically detectable interaction with the effects of nitroglycerin (FIGS. 2 and 3). The increase in radial artery diameter was maintained during the 2-hour application. In addition, the systemic blood pressure (mean arterial pressure) did not change, indicating a lack of systemic effect from topical application of nitroglycerin and lidocaine (FIG. 4).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for locally increasing arterial diameter and providing local anesthesia in a subject, the method comprising applying to a skin site of the subject a topical composition comprising a vasodilation agent in an amount ranging from 22.5 mg to 75 mg and an anesthetic agent in a manner sufficient for locally increasing diameter and providing local anesthesia in the subject without producing a significant systemic effect in the subject, wherein the vasodilation agent is nitroglycerin and the anesthetic agent is lidocaine.

2. The method of claim 1, wherein the artery is a radial artery of the subject.

3. A method for inserting a cannula into an artery of a subject, the method comprising:
   applying to a skin site of the subject a topical composition comprising a vasodilation agent in an amount ranging from 22.5 mg to 75 mg and an anesthetic agent in a manner sufficient for locally increasing arterial diameter and providing local anesthesia in the subject without producing a significant systemic effect in the subject; and
   inserting the cannula into the artery of the subject,
   wherein the vasodilation agent is nitroglycerin and the anesthetic agent is lidocaine.

4. The method of claim 3, wherein the artery is a radial artery of the subject.

5. The method of claim 3, wherein the applying is for a period of time of 30 minutes or more.

6. A topical composition for locally increasing arterial diameter and providing local anesthesia in a subject, the topical composition comprising:
   a vasodilation agent in an amount sufficient for locally increasing arterial diameter in the subject and ranging from 22.5 mg to 75 mg; and
   an anesthetic agent in an amount sufficient for providing local anesthesia in the subject, wherein the vasodilation agent is nitroglycerin and the anesthetic agent is lidocaine, and wherein the amounts of the vasodilation agent and the anesthetic agent are sufficient for locally increasing arterial diameter and providing local anesthesia in the subject without producing a significant systemic effect in the subject.

7. The topical composition of claim 6, wherein the topical composition comprises a lotion, cream, paste, ointment, gel or foam.

8. The topical composition of claim 6, wherein the topical composition comprises a transdermal patch.

9. The topical composition of claim 8, wherein the transdermal patch comprises an active agent layer.

10. The topical composition of claim 9, wherein the active agent layer comprises a mixture comprising the vasodilation agent and the anesthetic agent.

11. The topical composition of claim 9, wherein the active agent layer comprises a first layer and a second layer, wherein the first layer comprises the vasodilation agent and the second layer comprises the anesthetic agent.

12. The topical composition of claim 8, wherein the transdermal patch further comprises a backing layer.

13. The topical composition of claim 8, wherein the transdermal patch further comprises an adhesive.

14. A kit for inserting a cannula into an artery of a subject, the kit comprising:
- a topical composition for locally increasing arterial diameter and providing local anesthesia in the subject, the topical composition comprising:
  - a vasodilation agent in an amount sufficient for locally increasing arterial diameter in the subject and ranging from 22.5 mg to 75 mg; and
  - an anesthetic agent in an amount sufficient for providing local anesthesia in the subject, wherein the vasodilation agent is nitroglycerin and the anesthetic agent is lidocaine, and
- wherein the amounts of the vasodilation agent and the anesthetic agent are sufficient for locally increasing arterial diameter and providing local anesthesia in the subject without producing a significant systemic effect in the subject; and a sterile cannula.

15. The kit of claim 14, wherein the topical composition comprises a transdermal patch.

16. The kit of claim 14, further comprising sterile packaging.

17. The kit of claim 14, further comprising a sterile wipe.

18. The topical composition of claim 6, wherein the amount of the vasodilation agent is from 22.5 mg to 60 mg.

19. The topical composition of claim 6, wherein the amount of the vasodilation agent is from 22.5 mg to 45 mg.

20. The topical composition of claim 6, wherein the amount of the vasodilation agent is from 22.5 mg to 37.5 mg.

21. The topical composition of claim 6, wherein the amount of the vasodilation agent is 30 mg.

22. The topical composition of claim 6, wherein the arterial diameter is associated with a radial artery of the subject.

\* \* \* \* \*